United States Patent [19]

Bizzini

[11] Patent Number: 4,594,336

[45] Date of Patent: Jun. 10, 1986

[54] THIOLATED POLYPEPTIDE COMPOUND DERIVED FROM A TETANUS TOXIN FRAGMENT, THE PROCESS FOR OBTAINING AND ITS APPLICATION

[75] Inventor: Bernard Bizzini, Paris, France

[73] Assignee: Institut Pasteur, Paris, France

[21] Appl. No.: 601,745

[22] Filed: Apr. 19, 1984

Related U.S. Application Data

[63] Continuation of Ser. No. 425,543, Sep. 28, 1982, abandoned, which is a continuation of Ser. No. 210,810, Nov. 26, 1980.

[51] Int. Cl.$^4$ .................. A61K 37/00; C07K 15/04
[52] U.S. Cl. ........................... 514/2; 530/807; 530/345; 530/387
[58] Field of Search ............... 260/112.5 R; 424/177

[56] References Cited

U.S. PATENT DOCUMENTS

| | | | |
|---|---|---|---|
| 3,111,512 | 11/1963 | Benesch et al. | 260/112.5 R |
| 4,029,765 | 6/1977 | Helting | 260/112.5 R |
| 4,201,770 | 5/1980 | Stevens | 424/177 |

OTHER PUBLICATIONS

T. B. Helting et al., J. of Biol. Chem. 252, 187–193 (1977).

*Primary Examiner*—Delbert R. Phillips
*Attorney, Agent, or Firm*—Frost & Jacobs

[57] ABSTRACT

The present invention relates to a new thiolated polypeptide compound derived from a fragment of tetanus toxin.

This thiolated polypeptide compound is constituted by the B-II$_b$ fragment of tetanus toxin to which at least one —SH group is directly or indirectly bound.

Application: neuropharmacological retrograde axonal transport agent for transporting a medicine to the central nervous system.

7 Claims, No Drawings

THIOLATED POLYPEPTIDE COMPOUND DERIVED FROM A TETANUS TOXIN FRAGMENT, THE PROCESS FOR OBTAINING AND ITS APPLICATION

This application is a continuation of application Ser. No. 425,543, filed Sept. 28, 1982, now abandoned, which is continuation of application Ser. No. 210,810, filed Nov. 26, 1980.

The present invention relates to a new thiolated polypeptide compound derived from a fragment of tetanus toxin, the process for obtaining this compound and the application of the latter, in particular as a neuropharmacological transport agent and as a specific labelling agent of neuronal cells.

With regard to the tetanus toxin itself or its anatoxin, it was already proposed to use them notably for obtaining vaccines or assay reagents. In order to illustrate this prior art following references will be cited:

FR patent for addition No. 74,16,936 published under No. 2,270,891, which relates to a process for obtaining vaccines by treatment of a toxic product with glutaraldehyde. This process consists in treating a toxic product with glutaraldehyde in effecting the polymerization of a limited number of molecules of said product and the detoxification of said product. In this process tetanus toxin may be used as toxic product.

FR patent application No. 77,29,186, published under No. 2,366,569, relates to an immunochemical process for assaying haptens, wherein are used a particle sensitized by an antibody, prepared by sensitizing fine particles by an antibody of the hapten to be assayed and a hapten-carrier conjugate. The carrier of this conjugate may be notably tetanus toxoid.

This hapten-carrier conjugate is used as reagent in an immunochemical process and also for immunization of an animal in order to obtain corresponding antibodies [see on page 4, lines 20 to 32].

The tetanus toxoid is therefore used as a carrier of the hapten in the body of the animal for obtaining antibodies. However, there exists no teaching in this FR patent about a particular fragment of tetanus toxin and its possible use as axonal transport agent for drugs.

GB Pat. No. 2,013,690 relates to an antigen for early pregnancy test and contraceptive vaccine. This antigen is obtained from the β-subunit of human chorionic gonadotrophin by reducing and cleaving of three, four, five or six of intrachain disulphide bounds of said β-subunit, alkylating of the thus reducing intrachain disulphide groups and isolating of the produced antigen. This antigen may be coupled with a protein or a hapten to enhance its immunological specificity. Tetanus toxoid is cited as suitable protein.

GB Pat. No. 1,492,445 relates to a composition comprising a conjugate of a subject-compatible immunogenic carrier and an immunochemically purified hormone derivative. The tetanus toxoid is used as carrier in this composition.

DE-OS patent application No. 1,617,880 relates to a process for obtaining bioactive organotrope substances, particularly drugs. This process consists in making a conjugate of a biologically active substance with organotrope receptive substances obtained from cellular membranes or antibodies. The toxins may be used as organotrope substances.

Furthermore, it was proposed to use thiolated proteins as drug carriers. Reference may be made to U.S. Pat. No. 3,171,831 which relates to thiolation of proteins by reaction with homocysteine thiolactone in the presence of a tertiary amine. The thiolated proteins thus obtained, for example gelatin, may be used as carriers for drugs. According to example 18 of this U.S. Pat. No. 3,171,831 the gelatin thus treated is used for encapsulating a pharmaceutical product which is sensitive to the acid environment of the stomach. The pharmaceutical product is therefore in this case not coupled with the thiolated protein but coated with it.

On the other hand, it was disclosed in FR patent application No. 76,37,367 published under No. 2,334,954 a reagent for immunoenzymatic determination. This reagent is composed by an antigen and an enzyme coupled by means of an ester of maleimidobenzoic acid and n-hydroxysuccinimide.

It is known that tetanus toxin is retrogradely transported to the central nervous system and the peripheral nervous system. In this respect, reference may be made to the article of BIZZINI et al. entitled: "An antigenic polypeptide fragment isolated from tetanus toxin: chemical characterization, binding to gangliosides and retrograde axonal transport in various neuron systems", which appeared in the "Journal of Neurochemistry", 1977, vol.28, pp 529–542, and to all the bibliographic references cited in this article.

Various studies have shown that tetanus toxin may be degraded or cleaved into several fractions or subunits. For example, COHEN et al. [The Journal of Immunology vol. 104, no 6 June 1970] have shown that the freezing-defreezing of the crude filtrate of *Clostridium tetani* culture results in a degradation of the molecule of tetanus toxin; the resulting degraded tetanus toxin is practically devoid of toxicity and has a flocculating power lower than the one of tetanus toxin.

BIZZINI and RAYNAUD have also studied the sub-units A-I, A-II, A-III and B-I, B-II and B-III of tetanus toxin. [C.R. Acad. Sc. Paris., t. 279, 1974 series D, pp. 1809–1811 and Annales of Pasteur Institute Paris 126, 159–176 (1975)]. French Pat. No. 74,36,622 (publication No. 2,249,679) discloses an immunogenic atoxic product obtained from tetanus toxin. This atoxic product is obtained by the treatment of tetanus toxin with a proteinase.

BIZZINI et al. have also isolated from frozen crude toxin a polypeptide fragment of the toxin which is identical, from the immunological point of view, to the above mentioned fragments A-II and B-II, but differs therefrom by its size and toxicity [see in this respect Journal of Neurochemistry, 1977, vol. 28, pp. 529–542]. This fragment, named B-II$_b$, which will be defined in more detail hereinafter, is capable of binding to the gangliosides and to the synaptic membranes with an affinity which is even greater than that of tetanus toxin.

Owing to this property, it is suggested in this article that this fragment could be employed for specifically transporting to the central nervous system chemotherapeutic agents or pharmacological agents for determining specific effects in the central nervous system.

However, up to the present time, it has not been found how to bind these chemotherapeutic or pharmacological agents to said B-II$_b$ fragment so as to, on one hand preserve the full activity of the agent to be transported to the central nervous system and, on the other hand, to preserve the binding property of the B-II$_b$ fragment to the receptors for the tetanus toxin in the central nervous system.

There has now been found a way of binding chemotherapeutic or pharmacological agents to the B-II$_b$ fragment while preserving its property of binding to the receptors for the tetanus toxin in the central nervous system.

Moreover, to the knowledge of the applicant, it is very difficult to separate the neuronal cells from the glial cells. It has been found that the new thiolated polypeptide compound according to the present invention could be employed as a specific labelling agent for the neuronal cells. Then, the separation of the labelled neuronal cells becomes easier with the techniques well-known to one skilled in the art, such as gel filtration, affinity chromatography and the like.

The thiolated polypeptide compound according to the present invention is constituted by the B-II$_b$ fragment of the tetanus toxin to which is bound at least one —SH group and has substantially the same properties of retrograde axonal transport and binding to the receptors of the tetanus toxin as the B-II$_b$ fragment itself.

In the compound of the invention, the —SH group or groups are directly or indirectly bound to the B-II$_b$ fragment. Generally, in view of the process for producing it, which implies a thiolation, the —SH groups will be bound by means of the residue of the thiolation agent. The thiolation agent is moreover bound to the B-II$_b$ fragment by —NH$_2$ groups born by it.

The B-II$_b$ fragment, from which the new thiolated polypeptide compound according to the present invention is derived, is a polypeptide of the tetanus toxin whose molecular weight is about 46,000.

The process for obtaining this B-II$_b$ fragment and the physicochemical and immunological properties thereof are described in detail in the aforementioned article by BIZZINI et al. (Journal of Neurochemistry, 1977, vol. 28, pp. 529-542).

It will be briefly recalled that this fragment was obtained by the process which comprises subjecting a frozen filtrate of *Clostridium tetani* culture (Harvard Strain No 6037 of the National Collection of Microorganism Cultures of Pasteur Institute) to the following steps:

1. ultrafiltration in order to remove the substances having a molecular weight lower than 10,000;
2. fractionating with ammonium sulphate;
3. gel filtration.

The B-II$_b$ fragment has the following physicochemical properties:

molecular weight of about 46,000;

it has a disulphide bridge and two non reactive free sulfhydryl groups;

the N-terminal groups are tyrosine and lysine;

its compsition in aminoacids is given in the following table I.

The B-II$_b$ fragment of the tetanus toxin has the same antigenic structure as the B-II fragment but differs therefrom by its specific toxicity. The immunological properties of the B-II$_b$ fragment compared with that of tetanus toxin and of the B-II fragment are gathered in the following table II.

TABLE I

AMINO ACID COMPOSITION OF THE B-II$_b$ FRAGMENT

| Amino acids | Amino acid (g/100 g protein) | Nitrogen (g/100 g protein) | Number of assumed residues | Calculated molecular weight | Amino acids extracellular to the toxin (g/100 g protein) |
|---|---|---|---|---|---|
| Tryptophan | 2.96 | 0.41 | 7 | 48293 | 1.63 |
| Lysine | 7.36 | 1.41 | 23 | 45678 | 10.42 |
| Histidine | 1.61 | 0.44 | 5 | 48185 | 1.34 |
| Amide | — | 2.21 | — | — | — |
| Arginine | 4.60 | 1.48 | 12 | 45444 | 3.94 |
| Aspartic acid | 21.87 | 2.30 | 76 | 46208 | 17.72 |
| Threonine | 5.17 | 0.61 | 20 | 46080 | 5.32 |
| Serine | 7.60 | 1.01 | 33 | 45606 | 6.59 |
| Glutamic acid | 7.83 | 0.74 | 25 | 46975 | 10.49 |
| Proline | 3.54 | 0.43 | 14 | 45528 | 4.22 |
| Glycine | 4.14 | 0.77 | 25 | 45325 | 3.30 |
| Alanine | 3.53 | 0.55 | 18 | 45432 | 3.21 |
| Semi-cystine | 0.95 | 0.11 | 4 | 50656 | 1.12 |
| Valine | 6.22 | 0.76 | 24 | 45192 | 4.78 |
| Methionine | 1.75 | 0.16 | 5 | 42630 | 2.29 |
| Isoleucine | 10.32 | 1.10 | 36 | 45756 | 11.02 |
| Leucine | 11.38 | 1.22 | 40 | 46120 | 10.05 |
| Tyrosine | 10.25 | 0.79 | 26 | 45942 | 9.79 |
| Phenylalanine | 5.80 | 0.49 | 16 | 45568 | 6.39 |
| Total | 116.88 | 16.99 | 409 | 46145 | 113.62 |

TABLE II

Comparison of the main immunological and toxic characteristics of the B-II$_b$ fragment with those of the B-II fragment and tetanus toxin.

| Compound | Ouchterlony test (antigenic structure) | Specific flocculating activity (LF/mgN) | LF/O.D. | LF/Lf | Specific Toxicity LD/mgN |
|---|---|---|---|---|---|
| toxin | 1(a,b) | 3150 | 423 | 2.5 × 10$^3$ | 7.8 × 10$^7$ |
| fragment B-II$_b$ | 1(b) | 11000 | 1000 | 0.05 | 555 |
| fragment B-II | 1(b) | 8200 | 825 | 8 | 6.6 × 10$^4$ |

The thiolated polypeptide compound according to the present invention is produced by thiolation of the B-II$_b$ fragment previously treated for eliminating the residual toxicity thereof.

The thiolation of the B-II$_b$ fragment can be carried out by conventional means permitting the introduction of —SH groups on a molecule comprising amino groups, but for the purposes of the invention, the means in question must not denature the axonal transport property and the binding property to the specific receptor of the tetanus toxin in the central nervous system, of the B-II$_b$ fragment.

By way of example, it will be indicated that the thiolation of the B-II$_b$ fragment can be achieved with the following thiolation agents:

4-methyl-mercaptobutyrimidate:

$$HS-(CH_2)_3-\underset{\underset{NH_2^+Cl^-}{\|}}{C}O-CH_3$$

(Biochemistry vol. 17 No 8, 1978)

2-iminothiolane (Schramm J. H. and Dölffer T. (1977) Z. Physiol. Chem. 358; 137–139)

N-acetylhomocysteine thiolactone (AHT) (see J. Am. Chem. Soc., 1960, 82, 565–571)

$$\begin{array}{c} S \\ H_2C \diagup \quad \diagdown C=O \\ H_2C -\!\!\!-\!\!\!- CH \\ \qquad\qquad | \\ \qquad\qquad NHCOCH_3 \end{array}$$

S-acetyl-mercaptosuccinic anhydride (AMS) (J. Am. Chem. Soc. 1959, 81, 3802–3803)

$$CH_3-CO-S-CH-C \diagup^O_{\diagdown O} \\ \qquad\qquad | \qquad\qquad \diagup \\ \qquad\qquad CH_2-C \diagdown_O$$

On the other hand, it will be indicated that the known processes of thiolation consisting of a dithiopyridylation step and a reduction step are unsuitable for the purposes of the invention. Indeed, the properties of axonal transport and binding of the thus thiolated B-II$_b$ fragment are modified in the course of the reduction step.

For example, the thiolation effected by reaction with the N-succinimidyl-3-(2-pyridyl-dithio)-propionate and by reduction of the dithiopyridylated compound so obtained, for example according to the procedure described by CARLSSON et al. [(Bioch. J. (1978) 173 723–724] is unsuitable for the purposes of the invention.

In order to be more precise, it will be indicated that the thiolated polypeptide compound according to the invention comprises one or more Z—SH groups, in which Z is the residue of the thiolation agent.

Thus, if one of the thiolation agents mentioned above is employed, Z then represents:

$$-\underset{\underset{NH_2^+,\,Cl^-}{\|}}{C}-(CH_2)_3-;\quad -CO-\underset{\underset{NH-CO-CH_3}{|}}{CH}-CH_2-CH_2-;$$

$$-\underset{\underset{CH_2-COOH}{|}}{CH}-CO-;\quad -\underset{\underset{NH}{\|}}{C}-(CH_2)_3-$$

The thiolation of the B-II$_b$ fragment is achieved on the NH$_2$ groups thereof.

The residual toxicity of the B-II$_b$ fragment can be previously removed, for example, by an immunoadsorption step on a CNBr-activated Sepharose 4B gel column to which the IgG fraction of the anti-Ibc serum is covalently bound. The B-II$_b$ fragment thus obtained is not toxic in the mouse at the dose of 1.9 mg.

It has been found that the thiolated polypeptide compound according to the invention is suitable as a neuropharmacological transport agent for transporting pharmacological or chemotherapeutic agents to the central nervous system.

In order to transport a medicine to the central nervous system by means of the agent according to the invention, this medicine must be bound to the thiolated polypeptide compound, employed as a transport agent, without of course modifying the pharmacological properties of the medicine or the binding property of the B-II$_b$ fragment to the specific receptors of the tetanus toxin in the central nervous system. "Medicine" is intended to designate according to the invention any substance having pharmacological properties, such as pharmacological agents, chemotherapeutic agents and the like. The medicines which may be bound according to the invention to the polypeptide compound employed as a neuropharmacological transport agent must have —NH$_2$ groups.

As examples of medicines which may be transported to the central nervous system by means of the thiolated polypeptide compound according to the invention, it may be mentioned: alkaline phosphatase, the A fragment of cholera toxin, the A fragment of diphtheria toxin, dipyrido-indoles according to French Pat. No. 77,11,148 and, generally, any medicine having —NH$_2$ groups.

It is known that the cholera toxin is bound to the GM$_1$ gangliosides of the intestine wall and that the A fragment is responsible for the increase in the cyclic AMP rate (cyclic adenosine-monophosphoric acid). On the other hand, in tetanus a decrease in the cyclic AMP proportion in the central nervous system is found. The conjugate according to the invention, formed by the thiolated polypeptide compound coupled to the A fragment, may be employed for controlling tetanus.

The dipyrido-indoles according to French Pat. No. 77,11,148 are chemotherapeutics of utility in the traitment of cancers. In this field, it is known that the metastases are due to the fact that the cancerous cells nestle in the central nerous system whence they migrate to other regions of the body where they develop tumors.

The development of the metastases could be avoided or reduced as soon as the means for destroying these cells in the central nervous system reach the central nervous system.

In the same way, the invention may be applied to the treatment of cerebral tumors.

The present invention consequently also relates to the means for coupling the thiolated polypeptide compound according to the invention to medicines.

The means for coupling the compound according to the invention and the medicines to be transported use at least a disulphide bridge or at least a sulfur irreversible link.

The present invention therefore also relates to B-II$_b$/-medicine conjugates comprising at least one disulphide bridge or at least one sulfur irreversible link.

It is known to prepare protein conjugates by formation of an intermolecular disulphide bridge. The formation of such an intermolecular bridge is achieved for example by reaction of a protein having thiol groups with a protein having dithiopyridyl groups.

For example, according to the process described by TE PIAO KING et al. [Biochemistry vol. 17 No 8, 1978], two different proteins may be coupled by first binding thiol groups to one of the proteins and 4-dithiopyridyl groups to the other protein and by reacting the resulting modified proteins under suitable conditions in order to form disulphide bridge and eliminating 4-thiopyridone. The thiol groups may be bound to one of the proteins by means of 4-methyl-mercapto-butyrimidate and the 4-dithiopyridyl groups to the other protein by means of, for example, 3-methyl-(4'-dithiopyridyl)propionimidate. This coupling process produces a protein-protein conjugate in which the fraction between the two proteins is symmetrical relative to the disulphide bridge.

According to CARLSSON et al. (Bioch. J., 1978, 173, 723-724) the thiol group can be introduced in one of the proteins by reaction of said protein with N-succinimidyl-3-(2-pyridyl-dithio)propionate and subsequent reduction; according to this process, the same reagent, namely the N-succinimidyl-3-(2-pyridyl-dithio)propionate, is used for introducing thiol and dithiopyridyl groups in the proteins. The resulting conjugate also has a binding fraction which is symmetrical relative to the disulphide bridge.

4-methyl-mercapto-butyrimidate has also been used for forming higher dimers and oligomers of proteins of 30S ribosome of *Escherichia Coli* (Biochemistry, 12, 3266-3273, 1973).

The conjugates thus obtained have many applications, for example as immunological assay reagents.

The coupling process according to the invention, of the thiolated polypeptide compound used as a neuropharmacological transfer agent with a medicine by means of disulphide bridge consists of the steps of:

(1) introducing dithiopyridyl groups in the medicine to be bound;

(2) reacting the medicine having the dithiopyridyl groups with the thiolated polypeptide compound according to the invention.

The reaction diagram of this coupling process may be represented in the following manner when the dithiopyridylation agent used in step 1 is N-succinimidyl-3-(2-pyridyl-dithio)propionate:

  (1)

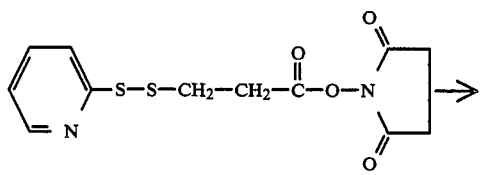

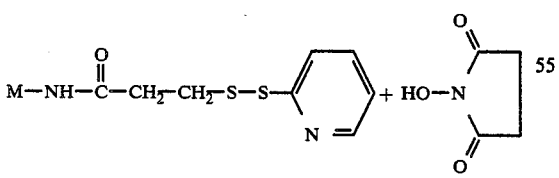

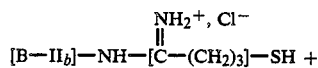  (2)

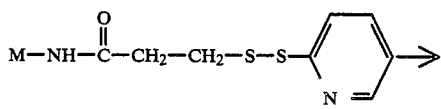

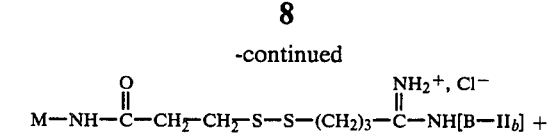

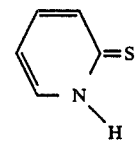

In this process, another dithiopyridylation agent may be employed, such as dithiopyridine or any other suitable agent for such a reaction.

Another way of coupling the polypeptide compound, used as a neuropharmacological treatment agent according to the invention, consists of creating an irreversible link between said agent and the medicine to be transported. This process may be represented by the following reaction diagram:

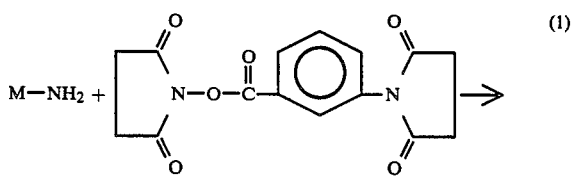  (1)

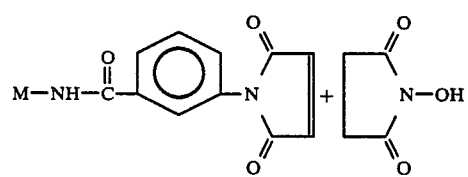

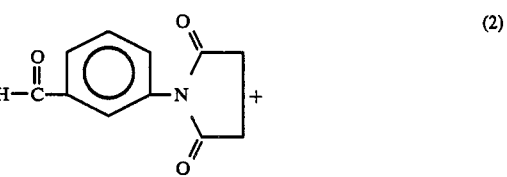  (2)

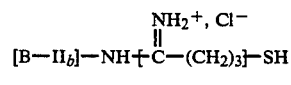

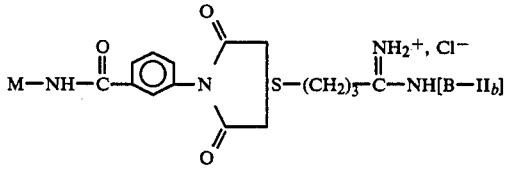

It consists of the steps of:

(1) reacting the medicine to be bound with the ester of metamaleimidobenzoyl-N-hydroxy-succinimide;

(2) reacting the resulting compound with the polypeptide compound according to the invention.

The foregoing reaction diagrams and those which will be given hereinafter are simplified and do not take into accound the number of SH groups which may be bound to the B-II$_b$ fragment.

It has already been proposed to use the ester of metamaleimidobenzoyl-N-hydrosuccinimide for forming enzyme-antibody conjugates (FEBS Letters, vol. 95, No. 2, November 1978). However, the teachings of this prior art did not permit foreseeing that the use of the ester of metamaleimidobenzoyl-N-hydrosuccinimide for coupling the neuropharmacological transport agent according to the invention to the medicines would not modify or inhibit the pharmacological properties of said medicines and the binding property of the B-II$_b$ fragment to the specific receptors of the tetanus toxin in the central nervous system.

It will be observed that the coupling according to the invention of the medicines to the thiolated polypeptide compound employed as a neuropharmacological transport agent is achieved by the known conventional techniques of protein-protein coupling. However, it should be noted that not all of the protein-protein coupling processes available to one skilled in the art are suitable for the purposes of the invention. Indeed, only the coupling processes which achieve a disulphide bridge or a sulfur irreversible link are suitable. In particular, it will be indicated that the most conventional coupling process which employs glutaraldehyde is unsuitable for the purposes of the invention, since the B-II$_b$ fragment treated with the glutaraldehyde loses its properties of axonal transport and binding to the receptors of the tetanus toxin in the central nervous system. Thus, the B-II$_b$ fragment to which carbonyl groups would have been bound, for example with glutaraldehyde, is unsuitable for the purposes of the invention.

Another application of the thiolated polypeptide compound according to the invention, is the labelling of neuronal cells. Thus, the compound of the invention may be employed as a specific labeller of neuronic cells and also for preparing immunological reagents. For example an enzymatic reagent may be prepared from the thiolated polypeptide compound according to the invention and alkaline phosphatase. It was found that the resulting conjugate had both the B-II$_b$ fragment binding power and the enzymatic activity of the phosphatase.

The invention will now describe in more detail by means of the examples illustrating the preparation of the thiolated polypeptide compound of the invention and of the coupling of the latter with medicines. In all the examples, there has been employed the B-II$_b$ fragment as defined hereinbefore devoid of its residual toxicity.

EXAMPLE 1

Thiolation of the B-II$_b$ fragment by means of 2-iminothiolane

The thiolation of the B-II$_b$ fragment was achieved by means of the method described by Schramm et al. [Z. Physiol. Chem. 1977, 358; 137–139].

The B-II$_b$ fragment (1 mg) in solution in 50% glycerol (0.2 ml) was thiolated by iminothiolane (0.5 mg) in solution in 750 μl of 0.2M triethanolamine HCl buffer, pH 8.5–9.0. The reaction mixture was maintained at room temperature for 2 hours. The excess of the reagent was eliminated by filtration on a "SEPHADEX G-25" column. The thiolated polypeptide product so obtained contained 1.2 —SH groups.

EXAMPLE 2

Thiolation of the B-II$_b$ fragment by means of N-acetylhomocysteine thiolactone The B-II$_b$ fragment was thiolated by the method described by SINGER et al. [J. Am. Chem. Soc., 1960 82, 567–571].

To 3 mg of the B-II$_b$ fragment in solution in 2 ml of water, there was added the K$_2$CO$_3$/NaHCO$_3$ buffer, pH 10.7 (1.6 ml). A nitrogen current was passed therethrough in order to expel the air. 0.4 ml of an 80 mg/l solution of N-acetylhomocysteine thiolactone was added. The reaction mixture was maintained for two hours at 4° C. under nitrogen. The reaction was thereafter stopped by filtration on SEPHADEX G 25. The obtained product contained 2.8 —SH groups.

EXAMPLE 3

Thiolation of the B-II$_b$ fragment by means of S-acetylmercaptosuccinimic acid anhydride The B-II$_b$ fragment was thiolated by the method described by Klotz et al. [J. Am. Chem. Soc., 1959, 81, 3802–3803].

The B-II$_b$ fragment (3 mg) was introduced into 1 ml of 0.1M phosphated buffer, pH 7.4, in a 3-necked flask and nitrogen was passed through the flask.

While stirring and maintaining a nitrogen atmosphere, 140 μg of S-acetyl-mercaptosuccinimic acid anhydride was introduced in two times at 5 minutes intervals.

The reaction was allowed to occur for a total of 20 minutes. The reaction mixture was then filtered on SEPHADEX G 25. A solution of the modified B-II$_b$ fragment was collected and 1M NH$_2$OH was added thereto until a final concentration of 0.1M was obtained. The deacetylation was allowed to occur for 5 minutes. The reaction mixture was then immediately filtered on SEPHADEX G 25 equilibrated with a 0.1M phosphate buffer, pH 7.4. The product so obtained had 5.6 —SH groups.

The reaction diagram may be represented as follows:

$$CH_3-CO-S-CH-C\underset{\underset{O}{\overset{\|}{CH_2C}}}{\overset{\overset{O}{\|}}{\underset{\|}{\big|}}}\begin{matrix}\nearrow O\\ \searrow O\end{matrix} + B-II_b \longrightarrow$$

$$[CH_3-CO-S-CH-CO]-B-II_b$$
$$\quad\quad\quad\quad\quad\quad\quad\quad | $$
$$\quad\quad\quad\quad\quad\quad CH_2-COOH$$

$$[CH_3-CO-S-CH-CO]-B-II_b + NH_2OH \longrightarrow$$
$$\quad\quad\quad\quad\quad\quad | $$
$$\quad\quad\quad\quad CH_2-COOH$$

$$[HS-CH-CO]-B-II_b$$
$$\quad\quad\quad | $$
$$\quad CH_2-COOH$$

EXAMPLE 4

Thiolation of the B-II$_b$ fragment by means of 4-methylmercaptonutyrimidate

The thiolation was carried out by the method described by TE PIAO KING et al. [Biochemistry vol. 17 No 8, 1978], by means of 4-methyl-mercaptobutyrimidate and a thiolated polypeptide compound was obtained comprising 1.4 groups of following formula:

$$-\underset{\underset{NH_2^+Cl^-}{\|}}{C}-(CH_2)_3-SH$$

EXAMPLE 5

Preparation of a thiolated polypeptide compound-A fragment of diphtheria toxin conjugate 2.2 mg of fragment A of diphtheria toxin in 1 ml of 0.025M borate buffer, pH 9.0, were employed. 7 mg of 2-iminothiolane and 77 μg of 4,4'-dithiopyridine were added in the form of a methanolic solution (100 μl of a solution of 3.85 mg in 5 ml of methanol). This solution was added in two times of 50 μl at 3 minutes intervals while cooling in ice and stirring. The reaction was allowed to occur for 2 hours. The reaction mixture was immediately applied to the SEPHADEX G 25 (0.9×20 cm) equilibrated with a 0.01M phosphate buffer, pH 6.9 containing 1 mM Na$_2$ EDTA.

Three moles of the polypeptide compound obtained from example 4 were mixed with 2.8 moles of the A-dithiopyridylated fragment according to the above method. The exchange reaction was followed at 324 nm. The mixture was filtered on SEPHAROSE 6 B equilibrated with a buffer tris 0.05M, 0.5M NaCl, pH 8.0.

The conjugate obtained preserves the binding power of the B-II$_b$ fragment and the immunological activity of the A fragment of the diphtheria toxin. Thus it is possible to prepare a chimera.

The dithiopyridylation of the A fragment may also be achieved by means of N-succinimidyl-3-(2-pyridyldithio)propionate.

EXAMPLE 6

Use of the thiolated polypeptide compound according to the invention as a neuropharmacological transport agent In order to show that the thiolated polypeptide compound according to the invention may be employed as a specific neuropharmacological agent, the peripheral oculomotor system in the rat was used as an experimental model.

The thiolated polypeptide compound obtained from the above example 4 was used. This thiolated polypeptide compound was coupled to the I$_{bc}$ fragment of the tetanus toxin.

The I$_{bc}$ fragment was obtained by papain digestion of the tetanus toxin.

The injection of this I$_{bc}$ fragment to mice produced symptoms of poisoning similar to those of the B fragment [Helting et al. J. Biol. Chem. 253, (1978) 125–129].

The I$_{bc}$ fragment coupled to the polypeptide compound according to the invention was used in order to show that it is the B-II$_b$ fragment which is bound to the specific receptors of the tetanus toxin in the central nervous system and not another fragment of the tetanus toxin, such as the I$_{bc}$ fragment. Indeed, the B-II$_b$/I$_{bc}$ conjugate comprising disulphide bridges obtained according to the coupling process defined above, resembles, from the structural point of view, the entire tetanus toxin, and the results mentioned below indicate that it is only the B-II$_b$ which is bound to the specific receptors of the tetanus toxin.

The B-II$_b$ and I$_{bc}$ fragments and also the B-II$_b$/I$_{bc}$ conjugate were labelled by means of $^{125}$I radioactive iode. This labelling was effected by the method of Greenwood et al. (*Biochem. J.* 89, (1963) 114–127).

For each substance to be labelled, there were employed 400 μg of said substance and 2 mCi of Na I$^{125}$ (provided by the Amersham Radiochemical Center).

The specific radioactivity of each substance thus labelled is indicated below:

| Substance | Radioactivity |
|---|---|
| B-II$_b$ fragment | 3.4 μCi/μg |
| I$_{bc}$ fragment | 2.6 μCi/μg |
| B-II$_b$/I$_{bc}$ conjugate | 3 μCi/μg |

Experiment procedure:

For all the experiments, female Sprague-Dawley rats weighing 250–270 g were used. The rats were maintained at a constant temperature of 23° C. and supplied with the usual diet (Nafag, Gossau) and water.

Five albino rats received an injection of one of the above labelled substances in the medial rectus muscle of the left eye according to the following procedure. After having bared the muscle, the substances were injected by a thermally controlled injection system by means of a glass pipette (50–100 μm outside diameter). The injecting time was 35 to 50 minutes. One rat received the above conjugate and the other four rats received one of the I$_{bc}$ or B-II$_b$ fragments. A 30% horseradish peroxidase (HRP type Sigma VI) was used as a control. The rats were sacrificed 24 hours after the injection. An intracardial perfusion was carried out under general anesthesia first of all with a plasma expander ("Macrodex"), then with 1.25% glutaraldehyde and 1% paraformaldehyde in 0.1M phosphate buffer, (pH 7.4) for 30 minutes, and lastly with a 10% sucrose in a 0.1M phosphate buffer (pH 7.4) for 30 minutes. For more details of this procedure, reference may be made to the article of MESULAM [J. Histochem. Cytochem., 26 (1978) 106–117].

The brain was removed immediately after this perfusion and placed in a 30% sucrose solution for 44 hours before cutting. Frozen sections (30 μm thickness) were taken, starting from the abducens nucleus and through the whole oculomotor nucleus. Each section treated with the horseradish peroxidase was stained by the TMB method of MESULAM and restained with neutral red while the other sections were autoradiographed. The latter sections were mounted and dipped into a liquid emulsion NTB$_2$ at 45° C. diluted 1:2 with distilled water. The sections were exposed for 4 weeks at 4° C. in the dark and developed with "Kodak Dektol" developer at 18° C. for 90 seconds, washed, and then fixed with 30% sodium thiosulfate, washed for 2 hours, then stained with cresyl violet and covered. All the sections were then examined under the microscope (250 magnification) and the location of the labelled cells was ascertained by microphotography.

In a first series of experiments, the B-II$_b$/I$_{bc}$ conjugate was injected simultaneously with the horseradish peroxidase in the medial rectus muscle and a radioactive labelling was found in the oculomotor nucleus for the conjugate and the horseradish peroxidase.

The main difference between the horseradish peroxidase (HRP) and the B-II$_b$/I$_{bc}$ conjugate resides in the fact that the location of the HRP granules is limited to the perikarya and dendrites of the oculomotor nucleus, while the silver grains which represent the $^{125}$I-labelled conjugate were also found in the pericellular spaces.

In another series of experiments, the $^{125}$I-labelled B-II$_b$ fragment was injected into two rats according to the above procedure and labelled cells were observed in neurons of the ipsilateral oculomotor nucleus in both the treated animals.

In a third series of experiments $^{125}$I-labelled $I_{bc}$ fragment and HRP were injected simultaneously into the eye muscle of a rat. This time, only a labelling of the cells of the oculomotor nucleus by the horseradish peroxidase was observed. In another animal, only the $^{125}$I-labelled $I_{bc}$ fragment was injected and no labelling of the cells of the oculomotor nucleus was observed. The fact that the experiment carried out with the first animals (treated simultaneously with HRP and $^{125}$I-labelled $I_{bc}$) gave positive results due to the HRP is important, since it shows that the fact that the $I_{bc}$ fragment was not transported in a retrograde axonal manner does not result from a breakdown of the retrograde axonal flow but rather from the specific properties of the $I_{bc}$ fragment which seem to be incompatible with intraaxonal transport functions.

Further, it was found that the $I_{bc}$ fragment does not bind to the gangliosides and isolated synaptic membranes. On the other hand, the B-$II_b$ fragment binds in a specific manner to the gangliosides and the synaptic membranes [see Journal of Neurochemistry (1977), vol. 28 p. 529-542].

The above test shows that if there is to be an axonal retrograde transport of a substance, the substance must be able to bind specifically to the gangliosides and synaptic membranes.

By means of the tests described in the Journal of Neurochemistry (1977) vol.28, p. 529-542, it was verified that the B-$II_b$/medicine conjugates obtained according to the invention from the thiolated polypeptide compound bound in a specific manner to the gangliosides and the synaptic membranes; these results demonstrate that the substances can consequently be transported in retrograde axonal manner.

TABLE III

Summary of the retrograde axonal transport experiments

| Experiments | Experiment reference | Radioactive labeller | Concentration (μg/μl) | Volume of the injection (μl) | Specific radioactivity (μCi/μg) | Animal sacrificed after | Retrograde transport |
|---|---|---|---|---|---|---|---|
| I | 79-477 | B-$II_b$/$I_{bc}$ conjugate | 3 | 1.44 | 3 | 24 hrs | + |
| | | HRP | 300 | 0.96 | — | — | + |
| II | 79-196 | $^{125}$I-B-$II_b$ fragment | 3 | 1.00 | 3.4 | 24 hrs | + |
| | 79-197 | $^{125}$I-B-$II_b$ fragment | 3 | 1.00 | 3.4 | 24 hrs | + |
| III | 79-480 | $^{125}$I-$I_{bc}$ fragment | 3 | 1.44 | 2.6 | 24 hrs | − |
| | | HRP | 300 | 0.96 | — | — | + |
| | 79-479 | $^{125}$I-$I_{bc}$ fragment | 3 | 2.40 | 2.6 | 24 hrs | − |

I claim:

1. A thiolated compound consisting of the B-$II_b$ fragment of tetanus toxin to which is covalently bound at least one Z—SH, wherein Z is the residue of a thiolation agent, said Z—SH having a formula chosen from the group consisting of:

-continued 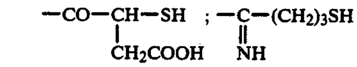 said compound being capable of being transported retrogradely along axons and to bind to the same receptors as tetanus toxin.

2. The compound of claim 1, wherein said B-$II_b$ fragment is previously treated so as to be devoid of residual toxicity.

3. A conjugate of the thiolated compound claimed in claim 1 with a pharmacological or therapeutical agent having $NH_2$ groups, the coupling resulting from the reaction of SH groups indirectly fixed to the B-$II_b$ fragments with dithiopyridyl or maleimido groups indirectly fixed to the N atoms of said agent.

4. A conjugate as claimed in claim 3 wherein the coupling part has the formula:

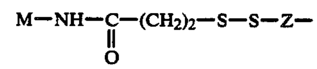

in which M is a part of said pharmacological or therapeutical agent and Z is selected from the group defined in claim 1.

5. A conjugate as claimed in claim 3, wherein the coupling part has the formula in which M is a part of said pharmacological or therapeutical agent and Z is selected from the group defined in claim 1.

6. A method of transporting a pharmacological or therapeutical agent to the central nervous system of a mammal which comprises administering to a mammal the conjugate of claim 3 in an effective amount.

7. A method of labelling neuronal cells without labelling glial cells which comprises administering to a mammal a compound as claimed in claim 1 in an effective amount.

* * * * *